United States Patent [19]

Noyori

[11] 4,281,148

[45] Jul. 28, 1981

[54] METHOD FOR THE PREPARATION OF A TRIORGANOSILYLATED 2,3-UNSATURATED ALCOHOL

[75] Inventor: Ryoji Noyori, Aichi, Japan

[73] Assignee: Shin-Etsu Chemical Co., Ltd., Tokyo, Japan

[21] Appl. No.: 186,212

[22] Filed: Sep. 11, 1980

[30] Foreign Application Priority Data

Sep. 18, 1979 [JP] Japan .................................. 54-119814

[51] Int. Cl.³ ................................................ C07F 7/18
[52] U.S. Cl. ..................................................... 556/470
[58] Field of Search ........................................ 556/470

[56] References Cited

U.S. PATENT DOCUMENTS 2,746,956  5/1956  Speier ............................. 556/470 X
2,766,103  10/1956  Nielsen et al. .................... 556/470 X
3,453,307  7/1969  Nitzsche et al. .................. 556/470 X

FOREIGN PATENT DOCUMENTS 738703  10/1955  United Kingdom ..................... 556/470

Primary Examiner—Paul F. Shaver

[57] ABSTRACT

The invention provides a novel method for the preparation of a triorganosiloxy derivative of a 2,3-unsaturated alcohol which is a useful intermediate compound for the synthetic preparation of various kinds of organic compounds. The method comprises reacting an oxirane compound having at least 3 carbon atoms in a molecule, of which the carbon atom adjacent to the oxirane ring has at least one hydrogen atom directly bonded thereto, with a triorganosilyl trifluoromethanesulfonate in the presence of an amine compound.

4 Claims, No Drawings

METHOD FOR THE PREPARATION OF A TRIORGANOSILYLATED 2,3-UNSATURATED ALCOHOL

BACKGROUND OF THE INVENTION

The present invention relates to a novel method for the preparation of a derivative of 2,3-unsaturated alcohols or, more particularly, of a triorganosilylated 2,3-unsaturated alcohol useful as an intermediate reactant of various organic compounds such as medicines, perfumes and the like.

As is well known, various types of derivatives of 2,3-unsaturated alcohols are widely used in the synthetic preparation of organic compounds. These derivatives of 2,3-unsaturated alcohols are obtained with an oxirane compound as the starting material by several known methods. For example, an oxirane compound is reacted with a dialkylaluminum amide (see, for example, Journal of the American Chemical Society, volume 96 (1974), page 6513) or a dialkylboron trifluoromethanesulfonate (see, for example, Chemical Letters, 1977, page 1215) as the reactant. The method using these reactants is applicable to a trans-2,3-dialkyl-substituted oxirane compound but is not applicable to the cis isomers and other ordinary cyclic oxirane compounds due to the decreased reactivity.

Alternatively, there has been proposed a method in which lithium amide which is a strong basic compound is used as the reactant (see, for example, Journal of the American Chemical Society, volume 82 (1960), page 6370 and Organic Syntheses, volume 53 (1974), page 17). This method is, however, hardly applicable to those oxirane compounds having an organic group less resistant to the attack of the base or those oxirane compounds having a cyclic structure susceptible to rearrangement.

Further alternatively, sodium phenylselenide has been proposed as a relatively mild reactant to be reacted with an oxirane compound (see, for example, Journal of the American Chemical Society, volume 95 (1973), page 2697) but this method is industrially practiced only with great difficulties due to the toxicity of selenium.

SUMMARY OF THE INVENTION

It is therefore an object of the present invention to provide a novel and improved method for the preparation of a derivative of an ethylenically 2,3-unsaturated alcohol useful as an intermediate compound of a synthetic preparation of various kinds of valuable organic compounds without the disadvantages or difficulties as described above in the prior art preparation.

Further object of the present invention is to provide a novel method for the preparation of a triorganosilylated or, in particular, trimethylsilylated 2,3-unsaturated alcohol useful as an intermediate compound of synthetic preparation of various organic compounds.

Thus, the method of the present invention for the preparation of a triorganosilylated 2,3-unsaturated alcohol comprises reacting an oxirane compound having at least 3 carbon atoms in a molecule of which the carbon atom adjacent to the oxirane ring has at least one hydrogen atom directly bonded thereto with a triorganosilyl trifluoromethanesulfonate in the presence of an amine compound.

DETAILED DESCRIPTION OF THE PREFERRED EMBODIMENTS

As is mentioned above, the method of the present invention comprises the reaction of an oxirane compound having at least 3 carbon atoms in a molecule of which the carbon atom adjacent to the oxirane ring has at least one hydrogen atom directly bonded thereto as represented by the general formula

in which $R^1$, $R^2$, $R^3$, $R^4$ and $R^5$ each denote a hydrogen atom or a monovalent hydrocarbon group or any combination of two of $R^1$ to $R^5$ may form jointly a divalent hydrocarbon group resulting in a ring structure, with a triorganosilyl trifluoromethanesulfonate represented by the general formula $$F_3CSO_3SiR_3, \qquad (II)$$

in which R is a monovalent hydrocarbon group, in the presence of an amine compound. The reaction between these reactants to form the desired triorganosilylated 2,3-unsaturated alcohol or triorganosiloxyalkene-2,3 is expressed by the following reaction equation.

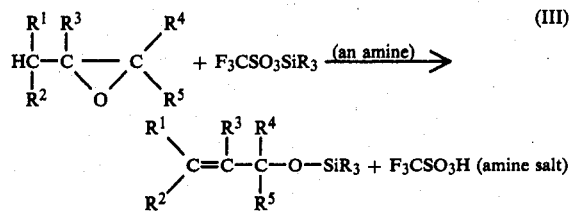

The starting oxirane compound must have at least 3 carbon atoms in a molecule since the desired product is a derivative of 2,3-unsaturated alcohol having 3 or more carbon atoms in a molecule as a matter of course. Further, the oxirane compound must have at least one hydrogen atom directly bonded to the carbon atom adjacent to the oxirane ring. The reason of this limitation is self-evident from the above given equation for the reaction with the triorganosilyl trifluoromethanesulfonate.

The groups denoted by the symbols $R^1$ to $R^5$ in the formula (I) may be each a hydrogen atoms or a substituted or unsubstituted monovalent hydrocarbon group. These groups must be sufficiently stable against the triorganosilyl trifluoromethanesulfonate and the undermentioned amine compound. When these groups are substituted hydrocarbon groups, the substituent atoms or groups may be or may include halogen atoms, amino groups, hydroxy groups, ether linkages, ester linkages, sulfide linkages, nitrile groups, ketone carbonyls and the like. In particular, hydroxy groups as the substituent in these groups are silylated by the reaction with the reactant of the formula (II).

Further, some of the groups $R^1$ to $R^5$ may be divalent groups so as that two of those divalent groups may form jointly a cyclic structure. For example, when $R^3$ and $R^4$ in the formula (I) jointly form a butene group $-(CH_2)_4-$, then the oxirane compound is a derivative of 1,2-epoxycyclohexane.

Particular examples of the oxirane compounds suitable for use as the starting reactant of the inventive method are named below by their chemical names or structural formulas: 1,2-epoxycyclopentane; 1,2-epoxycyclohexane; 1,2-epoxycycloheptane; 1,2-epoxycyclododecane; 1-methyl-1,2-epoxycyclohexane; 2,3-dimethyl-2,3-epoxybutane;

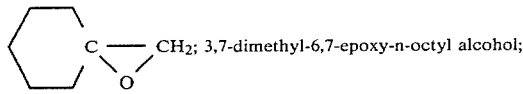

2,6-dimethyl-5,6-epoxy-n-heptyl methyl ketone; methyl 3,7-dimethyl-6,7-epoxy-n-octoate; trans- and cis-2,3-epoxycitronellols of the formula

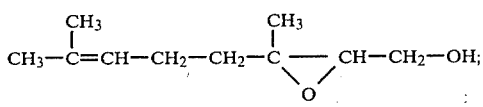

2-methyl-1,2-epoxypropane; and the like.

The triorganosilyl trifluoromethanesulfonate as the reactant to be reacted with the oxirane compound is a well known compound in the organosilicon chemistry as a sillylating agent. The triorganosilyl groups may be conventional ones and may be a phenyldimethylsilyl group, trimethylsilyl group, tert-butyldimethylsilyl groups and the like according to need.

The amine compound is used as a reaction accelerator or an acid acceptor. Suitable amine compounds are exemplified by triethylamine, tripropylamine, triphenylamine, 2,6-lutidine, 2,3-lutidine, aniline, methylpyridines, triazines, diaza-bicyclotriethylenediamine, 1,8-diaza-bicyclo(5,4,0)undecene-7 and the like. These amine compounds may be used either singly or as a combination of two kinds or more according to need. Particularly preferred amine compounds are the compound named last and lutidines.

The molar ratio of the reactants is preferably such that from 1.0 to 1.5 moles of the triorganosilyl trifluoromethanesulfonate of the formula (II) is reacted with 1 mole of the oxirane compound of the formula (I). It should be noted that, when the oxirane compound has one or more of hydroxy groups, the sulfonate compound is also reacted with these hydroxy groups so that an excess amount of the sulfonate compound should be formulated in the reaction mixture to balance the consumption by the hydroxy groups.

The amine compound as the reaction accelerator is usually used in an amount of 1 to 5 moles per mole of the oxirane compound. The reaction temperature should be varied widely according to the reactivity of the reactants as combined as well as the kind of the amine compound. It is usually in the range from −78° C. to +80° C.

The reaction is preferably carried out under an atmosphere of an inert gas such as argon and nitrogen and, if necessary, the reaction mixture may be diluted with an organic solvent with an object to moderate the reaction or to facilitate handling of the reaction mixture after completion of the reaction. Suitable solvents include, for example, benzene, toluene, xylene, hexane, cyclohexane, tetrahydrofuran, diethyl ether and the like. The reaction is complete usually within 30 minutes to several tens of hours depending on the particular combination of the reactants and the reaction conditions.

According to the method of the invention, the reaction can proceed under very mild conditions and the desired triorganosiloxy derivative of the 2,3-unsaturated alcohol is obtained in a high yield regardless of the type of the oxirane compound including di-, tri- and tetra-substituted oxirane compounds and cyclic oxirane compounds. The product compound of the inventive method has a Si—O—C linkage so that it is readily converted into a corresponding 2,3-unsaturated alcohol or it is a highly reactive intermediate compound in the synthesis of various kinds of organic compounds, for example, having biological activities.

In the following, the method of the present invention is described in further detail by way of examples, in which DBU, LU, Me and TMS denote 1,8-diaza-bicyclo(5,4,0)undecene-7, 2,6-lutidine, methyl group and trimethylsilyl group, respectively.

EXAMPLE 1

Into a solution of 2.26 g (0.0102 mole) of trimethylsilyl trifluoromethanesulfonate in 20 ml of benzene was added dropwise a mixed solution of 1.06 g (0.0107 mole) of 1,2-epoxycyclohexane and 2 ml of DBU in 5 ml of benzene at room temperature under an atmosphere of argon. After further agitation for 20 hours at room temperature, the reaction mixture was subjected to column chromatography with silica gel treated with ammonia as the adsorbent. Subsequent distillation of a chromatographic fraction gave 1.51 g of 3-trimethylsiloxycyclohexene boiling at 50° to 60° C. under a pressure of 50 mmHg. The yield was about 87% of the calculated value.

EXAMPLES 2 to 13

Twelve kinds of trimethylsiloxy derivatives of 2,3-unsaturated alcohols were prepared from the oxirane compounds as indicated in Table 1 below. The procedure of the preparation was substantially the same as in Example 1 using each 1 mole of the oxirane compound. DBU or LU was used as the amine compound in an amount indicated in the table. The temperature and time of reaction and the % yield of the products are also given in the table.

TABLE 1

| Exp. No. | Oxirane compound | Amine compound (moles) | Reaction Temp., °C. | Reaction Time, hours |
|---|---|---|---|---|
| 2 | 1,2-Epoxycyclopentane | DBU (1) | 29 | 5 |
| 3 | 1,2-Epoxycycloheptane | DBU (1) | 22 | 14 |
| 4 | 1,2-Epoxycyclododecane | DBU (1) | 27 | 40 |
| 5a | 2,3-Dimethyl-2,3-epoxybutane | LU (1) | −78 | 4 |
| 5b |  | DBU (1) | 24 | 3 |
| 6a | 1-Methyl-1,2-epoxycyclohexane | LU (1) | −78 | 3 |
| 6b |  | DBU (1) | 24 | 3 |

TABLE 1-continued

| Exp. No. | | Reagent | Temp. | Time |
|---|---|---|---|---|
| 7a | (cyclohexane-spiro-oxirane: C(CH₂)O with cyclohexyl) | LU (1) | −78 | 3 |
| 7b | | DBU (1) | 30 | 14 |
| 8a | 2-Methyl-1,2-epoxypropane | LU (1) | −78 | 10 |
| 8b | | DBU (1) | 13 | 0.5 |
| 9a | Me₂C(O)CH—CH₂CH₂CH(Me)CH₂CH₂—OH | LU (2) | −78 | 5 |
| 9b | | DBU (2) | 28 | 4 |
| 10a | Me₂C(O)CH—CH₂CH₂CH(Me)CH₂C(O)Me | LU (1) | −78 | 4 |
| 10b | | DBU (1) | 20 | 0.5 |
| 11a | Me₂C(O)CH—CH₂CH₂CH(Me)CH₂COMe | LU (1) | −78 | 4 |
| 11b | | DBU(1) | 15 | 2 |
| 12a | trans-2,3-Epoxycitronellol | LU (2) | −78 | 5 |
| 12b | | DBU (2) | 30 | 54 |
| 13a | cis-2,3-Epoxycitronellol | LU (2) | −78 | 3 |
| 13b | | DBU (2) | 32 | 14 |

| Exp. No. | Product compound | Yield, % |
|---|---|---|
| 2 | 3-Trimethylsiloxycyclopentene | 59 |
| 3 | 3-Trimethylsiloxycycloheptene | 40 |
| 4 | 3-Trimethylsiloxycyclododecene | 38 |
| 5a | 3-Trimethylsiloxy-2,3-dimethyl-butene | 87 |
| 5b | | 87 |
| 6a | cyclohexyl with =CH₂ and O—TMS | 80 |
| 6b | | 80 |
| 7a | cyclohexyl—CH₂—O—TMS | 72 |
| 7b | | 72 |
| 8a | 3-Trimethylsiloxy-2-methylpropene | 62 |
| 8b | | 62 |
| 9a | CH₃—C(=CH₂)—CH—CH₂CH₂CH(Me)CH₂CH₂O—TMS, O—TMS | 71 |
| 9b | | 71 |
| 10a | Me—C(CH)—CH—CH₂CH₂CH(Me)CH₂CMe(O), O—TMS | 69 |
| 10b | | 69 |
| 11a | Me—C(=CH₂)—CH—CH₂CH₂CH(Me)CH₂COMe(O), O—TMS | 79 |
| 11b | | 79 |
| 12a | Me—C(Me)=CH—CH₂CH=C(Me)—CH—CH₂O—TMS, O—TMS | 66 |
| 12b | | 66 |
| 13a | Me—C(Me)=CH—CH₂CH=C(Me)—CH—CH₂O—TMS, O—TMS | 16 |
| 13b | Me—C(Me)=CH—CH₂CH₂—C(=CH₂)—CH—CH₂O—TMS, O—TMS | 16 |

What is claimed is:

1. A method for the preparation of a triorganosilylated 2,3-unsaturated alcohol which comprises reacting an oxirane compound having at least 3 carbon atoms in a molecule, of which the carbon atom adjacent to the oxirane ring has at least one hydrogen atom directly bonded thereto, with a triorganosilyl trifluoromethanesulfonate in the presence of an amine compound.

2. The method as claimed in claim 1 wherein the amine compound is selected from the group consisting of triethylamine, tripropylamine, triphenylamine, 2,6-lutidine, 2,3-lutidine, aniline, methylpyridines, triazines, diaza-bicyclotriethylenediamine and 1,8-diaza-bicyclo(5,4,0)undecene-7.

3. The method as claimed in claim 1 wherein the amount of the triorganosilyl trifluoromethanesulfonate is in the range from 1.0 to 1.5 moles per mole of the oxirane compound.

4. The method as claimed in claim 1 wherein the amount of the amine compound is in the range from 1 to 5 moles per mole of the oxirane compound.